United States Patent [19]

Macfarlane

[11] Patent Number: 5,010,183

[45] Date of Patent: Apr. 23, 1991

[54] PROCESS FOR PURIFYING DNA AND RNA USING CATIONIC DETERGENTS

[76] Inventor: Donald E. Macfarlane, 943 Iowa Ave., Iowa City, Iowa 52240

[21] Appl. No.: 376,709

[22] Filed: Jul. 7, 1989

[51] Int. Cl.$^5$ .................... C07H 21/00; C07H 21/02; C07H 21/04
[52] U.S. Cl. ........................................ 536/27; 536/28; 536/29; 435/262; 935/19; 935/20
[58] Field of Search ............................ 536/27, 28, 29

[56] References Cited

U.S. PATENT DOCUMENTS

| | | | |
|---|---|---|---|
| 3,152,116 | 10/1964 | Broida | 536/27 |
| 3,157,637 | 11/1964 | Khym | 536/27 |
| 3,845,033 | 10/1974 | Harnden | 536/27 |
| 4,018,916 | 4/1977 | Hodge | 536/27 |
| 4,833,239 | 5/1989 | DeBonville et al. | 536/27 |
| 4,843,155 | 1/1989 | Chomczynski | 536/27 |

OTHER PUBLICATIONS

J. F. Robyt et al., Biochemical Techniques, Theory and Practice, Brooks/Cole Publishing Co., Monterey, CA, 1987, pp. 254–255.
Robinson, "The Organic Constituents of Higher Plants", 5th ed, Cordus Press, Ninth Amherst, MA, 1983, see pp. 270–272.
Davis et al., "Rapid DNA Isolation for Enzymatic and Hybridization Analysis", Ch. 49 in vol. 65.
"Methods in Enzymology" Grossman et al., eds., Academic Press, New York, New York, 1980, see pp. 404–411, esp. p. 405.
Perbal, "A Practical Guide to Molecular Cloning", John Wiley & Sons, New York, New York, 1984, pp. 152–159, esp. pp. 158–159.
Weil et al., Biochem. Biophys. Acta., 55:836–840 (1962).
Weil et al., Nature, 4798(192):169 (1961).
Jones, Biochem. et Biophys. Acta., 10;607–612 (1953).
Jones, Nature, 199:280 (1963).
Manfioletti et al., Nucleic Acids Research, 7(16):2873–2884 (1988).
Ralph et al., Biochem. Biophys. Acta., 87:9–16 (1964).
Aubel-Sadron et al., Biochem. Biophys. Acta., 53:11–18 (1961).

Primary Examiner—Johnnie R. Brown
Assistant Examiner—L. Eric Crane
Attorney, Agent, or Firm—Howson & Howson

[57] ABSTRACT

A novel method is provided for purifying DNA and RNA from a variety of sources, including cells, cell lysates, viruses, tissues, blood and other body fluids employing a cationic detergent to complex with the nucleic acids.

24 Claims, No Drawings

PROCESS FOR PURIFYING DNA AND RNA USING CATIONIC DETERGENTS

BACKGROUND OF THE INVENTION

Deoxyribonucleic acid (DNA), and ribonucleic acid (RNA), polymers of nucleic acids arranged in a particular order which contain inheritable genetic information, are employed in a wide variety of research, medical, diagnostic and industrial processes. The variety of uses for extracted and purified DNA and RNA from disparate sources is rapidly increasing with the advent of biotechnology as an industry for the production of pharmaceutical, agricultural, pesticidal and other agents. Additionally nucleic acid sequences are being increasingly employed for their ability to detect and identify genetic and familial disorders and carrier states; genetic aberrations found in tumors; and proof of identity or parentage. Nucleic acid sequences are also being employed to aid in the detection of infections by bacteria, viruses and other agents.

The production of genetically engineered proteins and polypeptides is another area where purified nucleic acid sequences are in demand. DNA and RNA are employed as starting materials in the manufacture of a variety of products, including nucleoside antibiotic and antiviral agents. DNA and RNA libraries and clones selected from them are also routinely employed in molecular biology and biotechnological research.

Generally nucleic acid sequences must be extracted from biological sources, e.g., tissue samples, bacteria, viruses, salmon sperm and the like, and purified by separation from proteins, salts and other biological molecules prior to use.

The standard procedure for isolating DNA from a cell source involves digestion with a combination of a proteolytic enzyme and a non-ionic or anionic detergent, such as sarcosyl or sodium dodecyl sulfate. The resulting digest is extracted with a mixture of phenol and chloroform, which removes most of the hydrolyzed products. The DNA is then precipitated from the resulting aqueous phase by the addition of alcohol.

For example, genomic DNA is extracted from eukaryotic cells by incubating them with a proteolytic enzyme (usually proteinase k) and the anionic detergent, SDS (sodium dodecyl sulfate). The resulting mixture is extracted with a mixture of phenol and chloroform, which leaves the DNA and RNA in the aqueous phase. The DNA is then precipitated by the addition of ethanol and sodium acetate, and resuspended in a buffer. RNase is then used to hydrolyse the RNA, and the DNA is collected by phenol/chloroform extraction and ethanol precipitation. Alternatively, cell nuclei can be prepared by dounce homogenization (or frozen pulverisation), filtration and centrifugation through sucrose. The nuclei are treated with proteinase K and SDS as above. Preparations of DNA should not contain impurities which inhibit the enzymes used to manipulate it further, such as restriction endonucleases or the Tag polymerase for use in the polymerase chain reaction. For some applications, the DNA should be very long. In these cases, DNA is prepared by the same general methods, but applied to cells imbedded in an agarose gel.

DNA in plasmids exists as double-stranded, closed circular DNA in the host bacteria. It is harvested by lysing the bacteria with lysozyme and a nonionic detergent. This liberates the plasmids, but leaves most of the bacterial DNA adherent to the cell debris, which can be removed by ultra-centrifugation. The plasmid is then separated by density-gradient ultra-centrifugation in the presence of ethidium bromide. Alternatively, the bacteria are treated with sodium hydroxide, and the plasmid DNA is separated by exclusion gel chromatography after RNase treatment.

DNA from bacteriophages or other viruses can be collected (after removing contaminating bacterial DNA with a DNase) by precipitation with polethylene glycol followed by extraction with chloroform/phenol and ethanol precipitation.

DNA is usually purified from reaction mixtures by chloroform/phenol extraction and ethanol precipitation. Spermine can be used to precipitate DNA, and can subsequently be removed by dialysis. DNA can be harvested by its binding to powdered glass in the presence of high salt solutions, or by adsorption and elution from commercially prepared columns.

The extraction of full length RNA requires methods that inhibit RNase's, which are ubiquitous. Cells can be ruptured by the addition of SDS in the presence of an RNase inhibitor, and extracted with phenol/chloroform followed by ethanol precipitation. Alternatively, cells can be lysed by the addition of guanidinium isothiocyanate followed by ultra-centrifugation through a cesium chloride gradient.

RNA is extracted by a variety of techniques designed to protect it from the action of RNAase's. One conventional method employs the chaptropic agent, guanidinium isothiocyanate, followed by ultracentrifugation to harvest the dense RNA. Another standard method for obtaining RNA from cell sources uses hot phenol extraction, followed by digestion of DNA with DNAase, extraction with phenol/chloroform, and precipitation with alcohol. In the intermediate steps of the processing of DNA, phenol/chloroform extraction and ethanol precipitation are often used.

The above-described nucleic acid extraction and purification techniques are described in detail in a number of standard molecular biology methodological texts, including T. Maniatis et al., "Molecular Cloning. A Laboratory Manual.", Cold Spring Harbor Laboratory, Cold Spring Harbor, N.Y. (1982) and L. G. Davis et al, "Basic Methods in Molecular Biology", Elsevier, N.Y. (1986).

A number of cationic detergents have been shown to be able to precipitate DNA and RNA from aqueous phases. Cationic detergents consist of a positively charged head group, which is usually a quaternary amine or a pyridinium group, and an aliphatic tail. Examples of commercially useful detergents include cetyl pyridinium bromide, cetyltrimethylammonium bromide (collectively known as cetrimonium compounds) and alkylbenzyldimethylammonium chlorides (collectively known as benzalkonium compounds). As the length of the side chain is increased, the resulting detergent become stronger, and its solubility in water decreases. Typical cationic detergents used in these procedures are cetyl pyridinium bromide, and cetyl trimethylammonium bromide, among others. See, e.g., A. S. Jones, Nature, 199:280–82 (1963); J. H. Weil and J. P. Ebel, Biochem. Biophys. Acta., 55:836–840 (1962). The ability of cationic detergents to precipitate DNA and RNA was reported by A. S. Jones, Biochem. Biophys. Acta.. 10:607 (1953). In a typical application, micro-organisms were extracted with phenol-p-aminosalicylate, and the DNA in the extract was precipitated with ethanol. The precipitate was dissolved in 1M NaCl (in which cytoplasmic RNA is insoluble), and the DNA was precipitated by the addition of cetyl trimethylammonium bromide (CTAB), after dilution to 0.55 to 0.60M NaCl. The DNA/CTAB complex was redissolved in 1M NaCl and reprecipitated with ethanol. The solubility of RNA and DNA complexes with cationic detergents in polar organic solvents was reported by French researchers. These cationic detergents included cetrimonium compounds and benzalkonium bromides, and the solvents included ethanol and formamide. These workers showed that the nucleotides could be precipitated from the organic solvent by the addition of sodium chloride. The ability of benzalkonium compounds to solubilise proteins at the same time as precipitating nucleotides was not mentioned. Other workers have reported similar findings.

There remains a need in the art for additional, simpler and more efficient methods for extraction and purifying nucleic acids from cell sources.

SUMMARY OF THE INVENTION

In one aspect the invention provides a method for purifying DNA or RNA from a mixture of biological materials, which comprises the step of adding a cationic detergent to a mixture containing the RNA or DNA in an amount sufficient to dissolve cells, solubilize any contaminating proteins and lipids in the mixture, and form insoluble hydrophobic complex between the nucleic acid and the detergent. The complex which comprises the RNA or DNA with the detergent is separated from the solubilized contaminants, and may be dissolved or dispersed in a polar organic solvent. Thereafter the DNA or RNA is recovered by the addition of a salt, which promotes the dissociation of the complex.

As another aspect of the present invention, there is provided a kit for use in performing the method of this invention comprising a quaternary amine cationic detergent. Additional optional components of the kit are one or more chaotropic, sulfhydryl-reducing or chelating agents, non-cationic detergents or hydrolytic enzymes.

Other aspects and advantages of the present invention are described further in the following detailed description.

DETAILED DESCRIPTION OF THE INVENTION

The present invention provides a novel method for purifying RNA and DNA from a mixture of biological materials. The biological material mixture may be intact cells. Alternatively, the mixture may be cell lysates, blood, viruses, other body fluids or other solutions containing DNA or RNA plus other contaminating molecules. This method is advantageously characterized by greater simplicity, speed and economy than prior art methods of nucleic acid purification. Additionally the process of this invention is less hazardous and more amenable to scale up or miniaturization than currently available methods.

The method of the present invention employs the step of treating a mixture of biological materials containing DNA or RNA with a cationic detergent to solubilize the contaminating proteins and lipids therein and cause the formation of a hydrophobic complex between the nucleic acids and the detergent.

Surprisingly, although some cationic detergents, e.g., cetyl pyridinium bromide, have been employed to precipitate DNA or RNA from aqueous media, the use of cationic detergents to directly treat the biological sources of nucleic acid to lyse cells and simultaneously precipitate RNA and DNA therefrom has not been described. Applicant has surprisingly discovered that a simpler, and more direct method of nucleic acid purification results from the use of a cationic detergent as a solubilizing agent.

According to the method of the invention, a cationic detergent is added to a mixture of biological materials containing nucleic acids. In practice of this invention to the biological mixture is added an aqueous solution in an amount sufficient to provide a final mixture comprising approximately 0.1 to 10% of the selected cationic detergent and from about 1 to 1000 $\mu$g nucleotide per ml. The detergent lyses the cells, and solubilizes contaminating lipids and proteins present in the mixture. The DNA and/or RNA in the mixture comprising the biological fluid and detergent solution form a hydrophobic complex with the detergent. This hydrophobic complex is then separated easily from the solubilized contaminants.

The cationic detergent selected for use in the method of the present invention is characterized by solubility in, or miscibility with, the extracting mixture. It must be a powerful detergent capable of lysing cells and solubilizing proteins and lipids. It is also capable of forming a hydrophobic complex with DNA or RNA, sufficiently strong to remain intact during the separation step. Further, the cationic detergent must not have deleterious effects, or contain impurities with such effects, on the subsequent processing of the RNA or DNA.

Presently preferred cationic detergents for use in the present invention are therefore quaternary amine detergents. Preferably, the detergent is an alkylbenzyldimethylammonium salt. More preferably, the detergent is an alkylbenzyldimethylammonium chloride, particularly where the alkyl group is linear and contains between 10 and 20 carbon atoms. The presently most preferred detergent is an alkyl-benzyl dimethyl-ammonium chloride, wherein the alkyl group contains 16 carbon atoms in a straight chain. This detergent, which is referred to hereafter as "16-BAC", can be prepared conventionally as a concentrated solution in water by techniques known to those of skill in the art. This detergent, also called benzyl dimethyl hexadecyl ammonium chloride, may be commercially obtained from Sigma Chemical Co., St. Louis, Mo. However other cationic detergents which fulfill the above-stated requirements may be selected for use in the practice of the invention by one of skill in the art.

The method of this invention may optionally include other steps such as adding to the mixture of biological materials, singly or in combination, one or more chaotropic, sulfhydryl-reducing or chelating agents, non-cationic detergents or hydrolytic enzymes. These optional components of the present invention may be added to the mixture before, during or after the addition of the cationic detergent. Alternatively, these optional components may be mixed with the cationic detergent prior to adding the detergent to the biological material.

The efficiency of the solubilization of contaminating substances may be enhanced in the method of this invention by the optional addition with the cationic detergent of a chaotropic agent to a final concentration in the biological mixture of about 0 to 60%. One typically employed agent is urea.

Another optional additive to the mixture undergoing the method of this invention is a sulfhydryl reducing agent, such as 2-mercaptoethanol or other known agents. A sulfhydryl reducing agent may be added to the mixture of biological materials to provide in a final concentration of about 0 to 2%.

A chelating agent, such as ethylenediaminetetraacetic acid (EDTA), may also be optionally used with the cationic detergent in this method to provide a concentration of from 0 to 2% in the final mixture.

The nucleic acid yield may be further increased by the addition to the mixture of hydrolytic enzymes, such as proteinase K, resulting in a final concentration of from 0 to 1% and/or non-cationic detergents, such as, Triton X100, resulting in a final concentration of from 0 to 10%, to disperse tissues before or during the addition of the cationic detergent.

According to the method, a hydrophobic complex of RNA or DNA with the detergent results upon treating the biological mixture with the detergent. This complex may be collected by centrifugation employing a force adequate to sediment the precipitate but not so large as to compress it into an intractable pellet. Such a centrifugation force increases as the content of the nucleotide decreases, and may desirably range from 100 xG to 15,000 xG for approximately 1 to 20 minutes. Precipitation may be enhanced by the addition of fine particles, such as silica gel.

Alternatively, the hydrophobic nucleic acid-cationic detergent complex may be separated from the solubilized contaminants by filtration. A conventional filter or matrix may be selected to capture the complexes without the use of excessive pressures. Illustrative filters for such use desirably have large pore sizes and may include Whatmann GF-A glass paper. The following standard matrices may also be employed in this separation step: gel filtration beads, hydrophobic beads, ion exchange beads, or hydrophilic beads.

The complexes can be washed with aqueous solutions to remove any residual contaminating substances. The hydrophobic nucleic acid-cationic detergent complexes are then dissociated by treatment with a suitable cation to liberate the DNA and RNA as their respective salts. This step involves dissolving or dispersing the complexes in a non-aqueous solvent, and then adding a suitable salt, which precipitates the RNA and DNA from the solvent, leaving the detergent in solution. Alternatively, the hydrophobic complexes may be dissociated and the RNA and DNA recovered by the addition to the complex of the salt without the prior dispersion or solution of the complexes in the solvent.

Many salts are capable of use in this dissociation step. Presently preferred salts are sodium chloride, sodium acetate, ammonium acetate. Although many solvents are suitable for this purpose, presently preferred solvents for use in this step of the method include ethanol, methanol and formamide and mixtures thereof. The dissociation steps takes approximately 5–120 minutes, with gentle stirring or agitation.

The method of this invention may be preferably performed, particularly for diagnostic purposes, such as the isolation of nucleic acids from a tumor biopsy sample, and other commercial purposes, by use of a kit providing the following minimal reagents required for the method. Such a kit includes specifically approximately 1 ml of solution of a selected cationic detergent, e.g., 16BAC, for use in treatment of approximately 10 mg of a tissue sample, solution, and the like. Approximately 10 ml each of a suitable solvent and a suitable salt solution for the dissolution step of the method are also included in the kit. Also part of such a kit are approximately 1 mg of an optional proteolytic enzyme, e.g., proteinase K for mixing with the biological fluid; an optional 0.1 ml of an anticoagulant for processing blood samples, and an optional 1 ml of a nonionic detergent solution for lysing cells. The kit may also comprise a container for mixing the biological fluid or tissue with the detergent and a suitable filter or matrix for the separation step. Other conventional components for diagnostic applications may also be included in a kit for performance of the method of the present invention.

The following examples illustrate performance of the method of the present invention, and are not intended to limit the scope of this disclosure.

EXAMPLE 1

Recovery of Genomic DNA Employing the Method of this Invention

Human leukemic blood cells (15 million HL-60 cells) were employed as the DNA source in this example. The cells were washed with Hanks solution and centrifuged to a pellet. To this pellet was added 5 ml of an aqueous solution containing 1% 16-BAC, 1% 2-mercaptoethanol, 10 mM EDTA, 4 M urea, and the resulting suspension was gently shaken. After standing for 15 minutes at room temperature, this mixture was centrifuged at 800 g for 10 minutes. The supernatant was discarded, and the pellet was washed by dispersing it in water and centrifuging it twice. The pellet was then dissolved in 0.7 ml ice cold ethanol by gentle agitation for 2 hours. Seven-tenths ml of ethanol saturated with ammonium acetate was then added, and the DNA and RNA was allowed to precipitate at $-20°$ C. for 2 hours.

The precipitate was dissolved in 0.5 ml 10 mM tris HCl pH 7.5, 15 mM NaCl, treated with RNAase and EcoR1 enzymes by conventional techniques. The yield of DNA was estimated by ultraviolet spectroscopy ($OD_{260}$) as 28, 47, 61, and 42 micrograms. The $OD_{260}/OD_{280}$ ratios were between 1.56 and 1.71. After electrophoresis through agarose, blotting to a filter and hybridization with a radioactive c-myc probe, the expected EcoRI-digested restriction fragment of the myc gene of 12.8 kb was detected by autoradiography.

EXAMPLE 2

Extraction of RNA Employing the Method of the Invention

HL-60 cells (15 million) were washed by centrifugation and resuspension in 5 ml of phosphate buffered saline. Five ml of an aqueous solution containing 2% 16-BAC, 40% urea, 2% 2-mercaptoethanol, and 20 mM EDTA was added to the suspension. The resulting mixture was centrifuged at 600 g for 5 minutes. The pellet was washed twice by resuspension in water and centrifugation, and then the pellet was extracted with 1 ml ethanol by vortexing for a few minutes. The mixture was centrifuged, and the supernatant was collected.

Fifty microliters of 3 M aqueous sodium acetate pH 5.2 and 400 microliters of water were added and the nucleotides were allowed to precipitate at $-20°$ C. overnight. After centrifugation, the pellet was dissolved in 20 microliters of RNAase free water. The yield of nucleotide (by $OD_{260}$) was 67 micrograms, $OD_{260}/OD_{280}=1.59$. Denaturing agarose gel electrophoresis (using formaldehyde) followed by elhidium bromide staining revealed fluorescent bands expected for undegraded rRNA. Northern blotting and hybridizing with a c-myc probe revealed c-myc mRNA.

EXAMPLE 3

Extraction of RNA from *E. coli* Employing the Method of this Invention

*E. coli* ($2.24 \times 10^9$ cells in 4 ml culture medium) were added to the 16-BAC extraction mixture of Example 2, and extracted following identical procedures. The yield of nucleotide, measured by $OD_{260}$, was 261 micrograms, $OD_{260}/OD_{280} = 1.92$. Denaturing agarose gel electrophoresis (using formaldehyde) followed by ethidium bromide staining revealed fluorescent bands expected for undegraded bacterial rRNA.

Numerous modifications and variations of the present invention are included in the above-identified specification and are expected to be obvious to one of skill in the art. For example, other appropriate sources of nucleic acids may be employed in the performance of the present method, as well as other optional agents. Such modifications and alterations to the compositions and processes of the present invention are believed to be encompassed in the scope of the claims appended hereto.

I claim:

1. A process for the purification of DNA and RNA from a biological mixture consisting essentially of applying directly to said mixture without prior purification or extraction of the nucleic acids a selected quaternary amine cationic detergent capable of simultaneously solubilizing contaminants in said mixture and forming a hydrophobic complex with said DNA or RNA in said mixture.

2. A proceeds for the purification of DNA and RNA from a biological mixture containing cells, lysed or intact, consisting essentially of applying directly to said mixture without prior purification or extraction of the nucleic acids a selected quaternary amine cationic detergent capable of simultaneously solubilizing contaminants in said mixture and forming a hydrophobic complex with said DNA or RNA in said mixture.

3. A process for the purification of DNA and RNA from a biological mixture containing virus consisting essentially of applying directly to said mixture without prior purification or extraction of the nucleic acids of selected quaternary amine cationic detergent capable of simultaneously solubilizing contaminants in said mixture and forming a hydrophobic complex with said DNA or RNA in said mixture.

4. The process according to claim 1 further consisting essentially of separating said hydrophobic complex from said contaminants.

5. The process according to claim 4 wherein said separating step consists essentially of centrifuging said mixture following the addition of fine particles of matter for facilitating precipitation of said complex.

6. The process according to claim 4 wherein said separating step consists essentially of collecting said complex on a surface or a matrix by filtration or absorption.

7. The process according to claim 1 further consisting essentially of dissociating said DNA and RNA from said complex to produce purified DNA and RNA.

8. The process according to claim 7 wherein said dissociating step comprises treating said complex with a salt in a non-aqueous solvent.

9. The process according to claim 1 wherein said detergent is an alkylbenzyldimethylammonium salt.

10. The process according to claim 9 wherein said detergent is an alkylbenzyldimethylammonium chloride, wherein said alkyl group consists essentially of from 10 to 20 carbon atoms.

11. The process according to claim 10 wherein said alkyl group consists essentially of 16 carbon atoms.

12. The process according to claim 1 further consisting essentially of adding to said mixture an chaotropic agent.

13. The process according to claim 1 further consisting essentially of adding to said mixture an sulfhydryl-reducing agent.

14. The process according to claim 1 further consisting essentially of adding to said mixture an chelating agent.

15. The process according to claim 1 further consisting essentially of adding to said mixture an non-cationic detergent.

16. The process according to claim 10 wherein said alkyl group consists essentially of 14 carbon atoms.

17. The process according to claim 10 wherein said alkyl group consists essentially of 18 carbon atoms.

18. The process according to claim 1 wherein said biological material consists essentially intact cells, cell lysates, blood, viruses, or other body fluids or solutions containing DNA or RNA.

19. A kit for isolating nucleic acids from a sample biological mixture containing nucleic acids in contaminating material consisting essentially of a cationic detergent in an amount sufficient to solubilize contaminants in said sample and form a hydrophobic complex with nucleic acids present in said sample.

20. The kit according to claim 19 wherein said detergent using a quaternary amine cationic detergent.

21. The kit according to claim 19 wherein said detergent is an alkylbenzyldimethylammonium salt.

22. The kit according to claim 21 wherein said detergent is an alkyl benzyldimethylammonium chloride.

23. The kit according to claim 22 wherein said alkyl group consists essentially of from 10 to 20 carbon atoms.

24. The kit according to claim 23 wherein said alkyl group consists essentially of 16 carbon atoms.

* * * * *

UNITED STATES PATENT AND TRADEMARK OFFICE
CERTIFICATE OF CORRECTION

PATENT NO. : 5,010,183
DATED : April 23, 1991
INVENTOR(S) : Donald E. Macfarlane It is certified that error appears in the above-identified patent and that said Letters Patent is hereby corrected as shown below:

Col. 3, line 2, delete "IM" and insert -- 1M --;

Col. 6, line 68, delete "elhidium" and insert -- ethidium --;

Col. 7, Claim 2, line 36, delete "proceeds" and insert -- process --.

Signed and Sealed this

Nineteenth Day of October, 1993

Attest:

BRUCE LEHMAN

*Attesting Officer*     *Commissioner of Patents and Trademarks*